United States Patent
Reichmuth (10) Patent No.: US 8,114,361 B2
(45) Date of Patent: Feb. 14, 2012

(54) METERING DEVICE

(75) Inventor: Burkhardt Reichmuth, Hamburg (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 12/749,731

(22) Filed: Mar. 30, 2010

(65) Prior Publication Data
US 2010/0266454 A1    Oct. 21, 2010

Related U.S. Application Data

(60) Provisional application No. 61/171,208, filed on Apr. 21, 2009.

(30) Foreign Application Priority Data

Mar. 31, 2009    (DE) .......................... 10 2009 016 590

(51) Int. Cl.
*B01L 3/02* (2006.01)
(52) U.S. Cl. ...... 422/501; 422/521; 422/522; 73/864.14
(58) Field of Classification Search .................. 422/501, 422/521, 522, 524, 525; 73/864.01–864.25
See application file for complete search history.

(56) References Cited

U.S. PATENT DOCUMENTS

| | | | | |
|---|---|---|---|---|
| 5,620,660 | A * | 4/1997 | Belgardt et al. | 422/525 |
| 5,620,661 | A * | 4/1997 | Sch urbrock | 422/525 |
| 6,540,964 | B2 * | 4/2003 | Kohrmann et al. | 422/501 |
| 7,563,409 | B2 * | 7/2009 | Suovaniemi et al. | 422/511 |
| 2006/0263261 | A1 * | 11/2006 | Lenz | 422/100 |
| 2009/0139351 | A1 * | 6/2009 | Reichmuth et al. | 73/864.11 |

FOREIGN PATENT DOCUMENTS

| | | |
|---|---|---|
| DE | 19830636 A1 | 1/2000 |
| EP | 2033712 A1 | 9/2008 |

* cited by examiner

*Primary Examiner* — Jan Ludlow
(74) *Attorney, Agent, or Firm* — Vidas, Arrett & Steinkraus, P.A.

(57) ABSTRACT

A metering device for utilization with a syringe, which features on a syringe cylinder a fastening portion with at least one axially directed sensing surface projecting from the upside, and at least one alignment nose projecting from the outer perimeter of the fastening portion, and a plunger with a plunger rod, the metering device having an accommodation for the fastening portion of the syringe cylinder, the accommodation having an axial opening for axially inserting the fastening portion into a fastening position, a sensing device disposed in the accommodation with at least one sensing means projecting from a basis surface of the sensing device facing the axial opening, for sensing the at least one sensing surface of a fastening portion inserted in a fastening position.

27 Claims, 7 Drawing Sheets

PRIOR ART

METERING DEVICE

CROSS-REFERENCE TO RELATED APPLICATIONS

This application claims priority to provisional U.S. patent Application No. 61/171,208, entitled Metering Device filed Apr. 21, 2009, the entire contents of which is incorporated herein by reference in its entirety.

STATEMENT REGARDING FEDERALLY SPONSORED RESEARCH

Not applicable.

BACKGROUND OF THE INVENTION

The present invention is related to a metering device for utilisation with a syringe.

Metering devices serve for metering liquids and are used in biological, chemical and medical laboratories in particular. In the realisation as dispensers, they permit the stepwise delivery of a liquid from a syringe. The metering amount per delivery step can be adjustable in this. A dispenser with metering amount adjustment is known from DE 29 26 691 C2, the entire contents of which is incorporated herein by reference.

Furthermore, pipettes are known as metering devices, by which an amount of liquid defined or adjustable via the apparatus can be picked up and delivered again in one procedure.

Syringes of different sizes are frequently provided for metering devices. These have in most cases different sizes of the cross section. In the transition to another syringe size, the once set metering amount does no more coincide with the real metering amount. Metering devices have therefore become known wherein the syringe has a code which is read by a sensing device of the pipette. An analysing unit can determine the utilised syringe size and indicate the metering amount that is effectively set.

A pipette system of the mentioned kind is known from EP 0 657 216 A2, the entire contents of which is incorporated herein by reference, and from U.S. Pat. No. 5,620,661 A, the entire contents of which is incorporated herein by reference. In this pipette system, the pipette has an accommodation for a fastening portion of a syringe in a pipette casing, and in an accommodation body it has a plunger accommodation for the syringe plunger of the syringe. Moreover, there are fastening devices for reversibly fixing fastening portion and syringe plunger in their accommodations, and plunger adjustment devices for displacing the accommodation body in the pipette casing. The syringe features an information carrier with information concerning the syringe and/or its condition, and the pipette has a sensing device for the information on the information carrier. Through axial openings in their accommodations, the fastening portion and the syringe plunger are axially shiftable into the pipette to their fastening positions, the information carrier arriving in a sensing position with respect to the sensing device through this. The syringe flange has an annular collar with at least one axially directed sensing surface with an axial position as information carrier, the syringe being insertable into the pipette in different rotational positions. The sensing device is made annularly with sensors distributed over the perimeter. The sensors have elastic, compressible knobs projecting from a front side of the sensing device that faces the axial openings. Preferably, there is an analysing unit for the information read by the sensing device and a display unit for the set metering amount. There are alignment noses on the fastening portion of the syringe and guiding grooves in the accommodation for the fastening portion for reproducible alignment of the syringe with its information carrier towards the sensing device. In a practical embodiment, the syringe has plural alignment noses uniformly distributed over the perimeter of the fastening portion, which are guided on axially directed bridges on a lateral border of the accommodation in order to direct the sensing surfaces towards the sensors. The alignment noses are each one chamfered at both sides on the upside, in order to guide the bridges into the grooves between the alignment noses in case that the same are not exactly directed towards the bridges.

The pipette system allows a user to utilise the syringe type according to the practical needs and to adjust the metering amount without sumptuous conversion work. The information may also concern other specific data of the syringe and/or of the condition of the syringe, for instance the purity condition or a filling material of the syringe, which are automatically taken into account by the pipette.

In spite of the essentially rotation-blocked mounting of the syringe in the accommodation by guiding the alignment noses in the guiding groove or on the axially directed bridges, respectively, the syringes can be rotated in the accommodation when an increased force is applied. This is due to the fact that the syringes are made of a plastic material like polypropylene, so that the alignment noses are deformed under load and may be pushed out of the guiding grooves or over the bridges, respectively. The sensing surfaces may laterally hit the projecting knobs of the sensing device when the syringe is rotated, and shear the same off with the electric contacts of the sensors, so that the metering device becomes unusable. The danger of destruction of the metering device is particularly high when a high-volume syringe is rotated in the accommodation which has an adapter with a fastening portion that is detachably connected to a syringe cylinder. Because this syringe has a relatively great diameter, relatively high torques can be introduced into the fastening of the syringe. The repair is sumptuous and comprises the exchange of the relatively expensive sensing device.

Starting from this, the present invention is based on the objective to provide a metering device that is protected against damage by distortion of a syringe.

BRIEF SUMMARY OF THE INVENTION

The metering device of the present invention for use with a syringe, which features on a syringe cylinder a fastening portion with at least one axially directed sensing surface projecting from the upper side and at least one alignment nose projecting from the outer perimeter of the fastening portion, and a plunger with a plunger rod, said metering device has an accommodation for the fastening portion of the syringe cylinder, with an axial opening for axially inserting the fastening portion into a fastening position, a sensing device disposed in the accommodation with at least one sensing means projecting from a basis surface of the sensing device facing the axial opening, for sensing the at least one sensing surface of a fastening portion inserted in a fastening position, at least one axial guiding means for adjusting the at least one alignment nose into an angular position with respect to rotation around the axis of the metering device, in which the syringe is axially directed towards at least one sensing means with at least one sensing surface, an accommodation body with a plunger accommodation and a further axial opening for axially inserting the plunger rod into a fastening position, fastening devices for detachably holding fastening portion and plunger rod in their fastening positions in the accommodations and in the plunger accommodation, and plunger adjustment devices for shifting the accommodation body, characterised in that the axial guiding mean is present in the accommodation below the sensing device, wherein the guiding means has a guiding contour on the side that faces the axial opening, said guiding contour has at least one indentation for receiving at least one alignment nose when the syringe is disposed with fastening portion and plunger rod being in their fastening positions, and the at least one raised part neighbouring the indentation has a distance from the basis surface of the sensing device greater about □h than the at least one indentation, wherein the syringe is adapted to be displaced with the at least one alignment nose to the at least one raised part from out the at least one indentation.

In the metering device of the present invention, by rotation around the symmetry axis of the cylinder-plunger system of the syringe which is inserted into the metering device, i.e. around the axis of the metering device, a syringe when being inserted is aligned by the co-operation of the alignment nose with the axial guiding means into an angular position in which each sensing surface of the syringe provided for this is axially directed towards a sensing means. In this, with its fastening portion formed on the cylinder and preferably being annular-shaped and located preferably at the upper end of the cylinder, and also with its plunger rod, the syringe arrives in the fastening position in which it is detachably held by way of the fastening device. The pipette can sense the sensing surfaces with its sensing device and acquire the information about the syringe and/or its condition that is contained in the number and/or the arrangement and/or the axial position of the sensing surfaces. This information may be processed and/or displayed via mechanical and/or electric and/or optical analysing units and/or via display units. Applying a great force it is possible to turn a syringe made of polypropylene or another soft elastic plastic material away from this fastening position without releasing the fastening means before, wherein each alignment nose is pressed along an associated guiding means under deformation. However, the present invention prevents that a damage of the preferably annular sensing device is accompanied by this. This is achieved by the preferably annular guiding means, which receives the at least one alignment nose in at least one indentation, provided that the syringe is correctly directed towards a sensing means with every sensing surface that is provided for this. When twisting the syringe, the at least one sensing surface slides from out the at least one indentation to the at least one raised surface which has a greater distance from the sensing device, so that the syringe cylinder is displaced away from the sensing device. In this, the sensing surfaces are displaced away from the annular sensing device, so that they do not damage the sensing means projecting from there and the sensing means are actuated no more. In the twisting, the fastening portion is preferably moved away from the annular sensing device so far that the sensing surfaces just no more touch the sensing means. Thus, the present invention takes the finding into account that a forced twisting of the syringe out of its fastening position in the metering device cannot be prevented due to the soft elastic plastic materials that are used for the syringe. However, the metering device of the present invention prevents damage of the expensive sensing device by having means which transform a rotation of the syringe with respect to the pipette into a shifting apart of fastening portion and sensing device.

According to one embodiment, the at least one axial guiding means has a guiding bridge and/or a guiding groove in the axial direction. Also, parallel axial guiding bridges can limit a guiding groove.

The information regarding the syringe and/or its condition may be contained in the number and/or arrangement and/or the axial position of one or plural sensing surfaces on the fastening portion of the syringe. Preferably, the sensing surfaces that characterise the syringe are all disposed in one single defined distance from the upside of the fastening portion, so that a binary representation of the information which excludes sensing errors as far as possible can be achieved by disposing or omitting sensing surfaces at a certain perimeter position of the fastening surface.

The present invention incorporates embodiments in which the annular sensing device has only one single sensing means. According to a preferred embodiment, plural sensing means are distributed over the perimeter of the sensing device. Through this, information can be read from a syringe having plural sensing surfaces that are distributed on the perimeter.

In a further embodiment, the metering devices of the present invention can also receive syringes which have a flat surface vertical to the axis of the syringe and so also to that of the metering device as a sensing surface, wherein this surface has local indentations which characterise the respective syringe type. The sensing means provided in the sensing device have to be positioned exactly opposite to these indentations in order to read this code. This is achieved by the guiding means when the at least one alignment nose of the syringe is received in the indentation of a guiding means. Now, the sensing means are designed such and the guiding means is dimensioned such that the sensing means are actuated only when the alignment noses sit in the indentations of the guiding means and the sensing surface facing the sensing means has no local indentation. Thus, the sensing means are released only there where the flat sensing surface is facing them. However, this code can be perceived by the sensing means only when the sensing surface is sufficiently approached by the sensing means through the insertion of the alignment noses into the guiding means of the sensing device. When the alignment noses of the syringe are not already in the indentation, any contact of the sensing means by the syringe is excluded. The sensing means can then not be actuated neither be damaged by a rotational movement of the syringe.

In another embodiment, the metering devices of the present invention can also receive syringes which have a flat surface vertical to the axis of the syringe and thus also to that of the metering device as a sensing surface, wherein this surface has local raised parts which characterise the respective syringe type. The sensing means provided in the sensing device have to be positioned exactly opposite to these raised parts in order to read this code. This is achieved by the guiding means when the at least one alignment nose of the syringe is received in the indentation of a guiding means. Now, the sensing means are designed such and the guiding means are dimensioned such that the sensing means are actuated only when the alignment noses sit in the indentations of the guiding means and the sensing surface facing the sensing means has a local raised part. Thus, the sensing means are released only there where a raised part of the otherwise flat sensing surface is facing them. However, this code can be perceived by the sensing means only when the sensing surface is sufficiently approached by the sensing means through the insertion of the alignment noses into the guiding means of the sensing device. When the alignment noses of the syringe are not already in the indentation, any contact of the sensing means by the syringe is excluded. The sensing means can then not be actuated neither be damaged by a rotational movement of the syringe.

In principle, the preferably annular sensing device may be disposed rigidly with respect to the accommodation. In a preferred embodiment, it is supported in the accommodation by way of at least one spring means acting axially against the displacement direction of the fastening portion. The spring means catches when the pipette is inserted. Through this, tolerances are compensated and damage of the sensing device is avoided.

Springy holding means can exist for the fastening portion, so that fastening portion and sensing device can be displaced away from each other when the syringe is rotated. For instance, the fastening devices can be realised in a springy fashion. Further, it is possible to make the fastening portion springy on locations that are held by the fastening devices. According to a preferred embodiment, the preferably annular guiding means is connected to the sensing device and is supported in the accommodation by way of the at least one spring means. In this embodiment, twisting of the syringe that is detachably held in the pipette results in a movement of the annular guiding means, accompanied by taking along the preferably annular sensing device, wherein the at least one spring means catches in. As a result, the sensing device evades from the sensing surfaces of the syringe and will not be damaged.

The springy realisation of sensing devices, and as the case may be of guiding means, facilitates the automatic separation of pipette and syringe after releasing the fastening means.

The fastening means can be realised differently. According to a preferred embodiment, the fastening means are radially feedable gripping equipments for fixing the fastening portion and the plunger rod in the fastening positions.

The present invention incorporates embodiments with only one indentation of the annular guiding means. According to a preferred embodiment, the annular guiding means has a guiding contour with several indentations distributed over the perimeter, and raised parts disposed between them. The insertion of the syringe into the pipette is facilitated through this. Preferably, the number of the indentations corresponds to the number of the sensing devices. Moreover, when the number of the sensing surfaces corresponds to the number of the sensing means, it is made sure that all the sensing surfaces are sensed by sensing means in every setting position of the syringe.

Gradual removal of the fastening portion from the sensing device when the syringe is rotated in the pipette can be made sure by a suitable contour of the alignment nose in particular. For this purpose, the alignment nose may be rounded or chamfered on both side at the upside. According to a preferred embodiment, the guiding contour gradually ascends between the indentations and the raised parts. This favours a smooth gliding of the alignment noses over the guiding contour in the rotation of the syringe, in particular in co-operation with rounded or chamfered sides of the at least one alignment nose. According to a further embodiment, the transitions between the indentations and the raised parts are ramp-shaped and/or rounded.

According to a preferred embodiment, all the indentations are on the same level with respect to the annular sensing device, and/or all the raised parts are on the same level with respect to the sensing device.

According to a further embodiment, the plunger adjustment devices are manually and/or motor driven. A manual plunger adjustment device is described in DE 29 26 691 C2, the entire contents of which is incorporated herein by reference, and in U.S. Pat. No. 4,406,170 A, the entire contents of which is incorporated herein by reference. The explanations relating to this are incorporated into the present application by reference.

According to a further embodiment, the metering device has an analysing unit and/or a display unit connected to the sensing device for the information read by the sensing device. The analysing unit can process the read-out information taking into account a metering amount setting of a plunger adjustment device in particular, and display the respective metering amount or the respective dispensing volume, respectively, on the display unit.

In principle, the metering device can be realised on a frame or another supporting structure. According to a preferred embodiment, the metering device has a casing which comprises the following components completely or partly: the accommodation, the sensing device, the axial guiding means, the accommodation body, the fastening means, the plunger adjustment devices, the guiding means, the analysing unit and the display unit.

According to one embodiment, the metering device is constructed such that it can be held by the hand when metering. According to a further embodiment, the metering device is a stationary metering device. It is also possible to design the metering device such that it can be selectively either held by hand or be operated as a stationary device. Further, the metering device can be made to be adapted for actuation by hand and/or automatically, that is to say, the metering processes can be controlled by hand and/or automatically. The metering device of the present invention may be a dispenser as well as a pipette.

The metering device of the present invention may be utilised with syringes whose syringe cylinder is connected in one piece with a fastening portion. It is also related to syringes where the fastening portion is formed on an adapter which is detachably connected to the syringe cylinder, for instance via a bayonet joint, a screw joint or a clamping joint. Adapters are used with high-volume syringes in particular. These may be syringes with a capacity of 25 ml or 50 ml in particular.

The metering device can have further features of the pipette system according to EP 0 657 216 A, the entire contents of which is incorporated herein by reference, for U.S. Pat. No. 5,620,661 A, the entire contents of which is incorporated herein by reference. This holds in particular for the design of the accommodation, of the sensing device, the axial guiding means, the accommodation body and the fastening means according to the aforementioned documents. In particular, the metering device may co-operate with syringes which are described in the aforementioned documents. The specifications concerning this in EP 0 657 216 A2 and U.S. Pat. No. 5,620,661 A are incorporated into the present application by reference.

In a preferred embodiment of the present invention, the guiding means of the metering device is annular and has an outer ring with an inside diameter $D_1$. On the side of this ring that faces the axial opening of the metering device, the guiding contour of the guiding means with its indentations and raised parts is situated. The sensing surface of the syringe and the sensing means of the sensing device are disposed within the outer ring of the guiding means.

The guiding means of the metering device of the present invention has preferably also abutment elements, which bear two-dimensionally against a basis surface of the sensing device. The basis surface is distinguished in that the sensing means of the sensing device are radially projecting from it. In this, the basis surface is preferably flat and particularly preferably it stands vertical to the symmetry axis of the cylinder-plunger system of the metering device. The guiding means are preferably annularly shaped in this. In a guiding means with an outer ring on which the guiding contour of the guiding means is situated, the abutment elements are preferably disposed within the outer ring having an inside radius $D_1$.

The metering device of the present invention is preferably constructed such that its fastening means can receive a syringe only then when the at least one alignment nose of the syringe is received in the at least one indentation of the guiding means. In order that a syringe is received by the fastening means, it has to be put into the syringe in particular such that the at least one spring means supporting the sensing device is compressed. Preferably, the guiding contour of the guiding means of the metering device is shaped such that the at least one alignment nose of the syringe is unavoidably moved into the associated indentation of the guiding means.

A metering device for utilisation with a syringe, which features on a syringe cylinder a fastening portion with at least one axially directed sensing surface projecting from the upside, and at least one alignment nose projecting from the outer perimeter of the fastening portion, and a plunger with a plunger rod, the metering device having an accommodation for the fastening portion of the syringe cylinder, the accommodation having an axial opening for axially inserting the fastening portion into a fastening position, a sensing device disposed in the accommodation with at least one sensing means projecting from a basis surface of the sensing device facing the axial opening, for sensing the at least one sensing surface of a fastening portion inserted in a fastening position, at least one axial guiding means for adjusting the at least one alignment nose into an angular position with respect to rotation around the axis of the metering device, in which the syringe is axially directed towards at least one sensing means with at least one sensing surface, an accommodation body with a plunger accommodation and a further axial opening for axially inserting the plunger rod into a fastening position, fastening devices for detachably holding fastening portion and plunger rod in their fastening positions in the accommodations and in the plunger accommodation, and plunger adjustment devices for shifting the accommodation body, wherein the axial guiding mean is present in the accommodation below the sensing device, wherein the guiding means has a guiding contour on the side that faces the axial opening, said guiding contour has at least one indentation for receiving at least one alignment nose when the syringe is disposed with fastening portion and plunger rod being in their fastening positions, and the at least one raised part neighbouring the indentation has a distance from the basis surface of the sensing device greater about Δh than the at least one indentation, wherein the syringe is adapted to be displaced with the at least one alignment nose from out the at least one indentation to the at least one raised part.

BRIEF DESCRIPTION OF EACH OF THE FIGURES OF THE DRAWINGS

The present invention will be explained in more detail below by way of the attached drawings, which show a preferred embodiment of an annular sensing device, an annular guiding means and an adapter. In the drawings show.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated In the present application, the indications "up" and "down", as well as "upside" and "downside" refer to the preferred alignment of the metering device in the operation, wherein the metering device is aligned vertically and a syringe connected to the metering device is disposed below the metering device.

Figure 1:
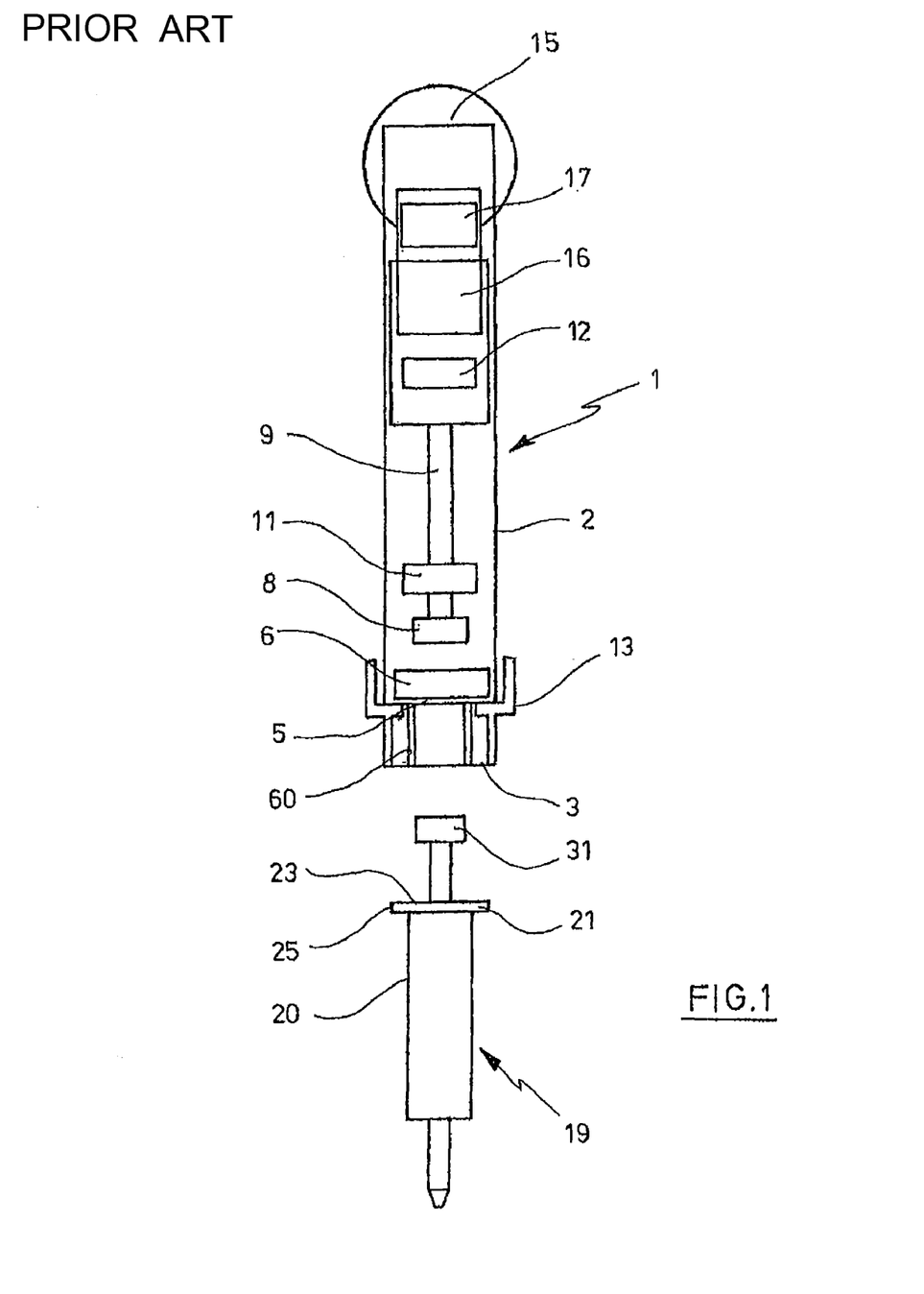
FIG. 1 a schematic view of the essential elements of a metering device according to the state of the art, with syringe separated from it, in a longitudinal section, FIG. 2 an adapter in an enlarged perspective view, slantly from the upside and from the side, FIG. 3 the syringe in a side view, FIG. 4 detailed view of the fastening portion of the syringe according to FIG. 3, FIG. 5 arrangement with an annular sensing device and an annular guiding means on a mounting plate in a perspective view, slantly from the upside and from the side, FIG. 6 an exploded view of the individual components of the arrangement according to FIG. 5, FIG. 7 a detail view of a region shown in FIG. 5, in particular of the guiding means of the metering device, FIG. 8 an adapter in the correct fastening position, held by gripping equipments in the arrangement of FIG. 3, in a side view, FIG. 9 the fastening portion of the adapter in the same position on the annular sensing device, omitting the annular guiding means and the gripping equipments, in an enlarged perspective partial view, FIG. 10 an adapter in an arrangement of FIG. 3, held in a twisted position by way of gripping equipments, in a side view, FIG. 11 the fastening portion of the adapter in the same position on the annular sensing device, omitting the annular guiding means and the gripping equipments, in an enlarged perspective partial view.

According to FIG. 1, a metering device 1 of the state of the art actuated by hand comprises a casing 2, which has an accommodation 3 at the downside, which is accessible from the outside through an axial opening 4 on the lower end.

The accommodation 3 has an approximately circular cross section.

An annular sensing device 6 is disposed on the bottom 5 of the accommodation 3.

On the side walls that laterally limit the accommodation 3, there are lateral guiding means 60 in the form of axially running ribs. In the example, three ribs are distributed over the perimeter of the accommodation 3.

Above the accommodation 3, an accommodation body 8 exists in the casing 2 of the metering device. The same is connected at its upper end with a driving rod 9 of plunger adjustment devices 10 for axially displacing the accommodation body 8 in the pipette casing 2. The plunger adjustment devices 10 feature a draw-up lever 11 for drawing up liquid for a syringe that is to be connected to the pipette 1. Further, they have a metering lever 12 for delivering liquid from a syringe.

Fastening devices 13 in the form of radially feedable gripping equipments for a syringe cylinder 13 and for a syringe plunger 14 (not shown) are associated to the accommodation 3 and the accommodation body 8. The fastening devices 13, 14 are realised as pivotally mounted gripping levers, which co-operate when a syringe is detached from the metering device 1.

On the upside of the casing of the metering device 2, there is an adjustment device 15 for am metering step width in the form of a little adjustment wheel, which is connected to the plunger adjustment devices 10. Furthermore, at the upside in the casing of the metering device 2 there is an analysing unit 16, which is connected to the sensing device 6 and the adjustment device 15, in order to determine the respective metering or dispensing volume, respectively, by way of the code of an inserted syringe detected by the sensing device 6 and the metering step width given by the adjustment device 15. The analysing unit 16 is connected to a display unit 17 in the form of a LCD display, disposed at the upside on the pipette casing 2, which displays the respective dispensing volume that is set. Further, the casing of the metering device 2 contains a power supply in the form of a battery or an accumulator.

An example for a pipette 1 with the features described above is described in EP 0 657 216 A2, the entire contents of which is incorporated herein by reference, and in U.S. Pat. No. 5,629,661 A, the entire contents of which is incorporated herein by reference. The specifications concerning this in the description of the figures of the above-mentioned documents are incorporated into the present application.

Besides, the metering device 1 of the present invention has an annular guiding means 7 at the bottom 5 of the accommodation 3 that concentrically surrounds the annular sensing device 6 and whose details and function will be described by way of the FIGS. 5 to 11.

Figure 3:
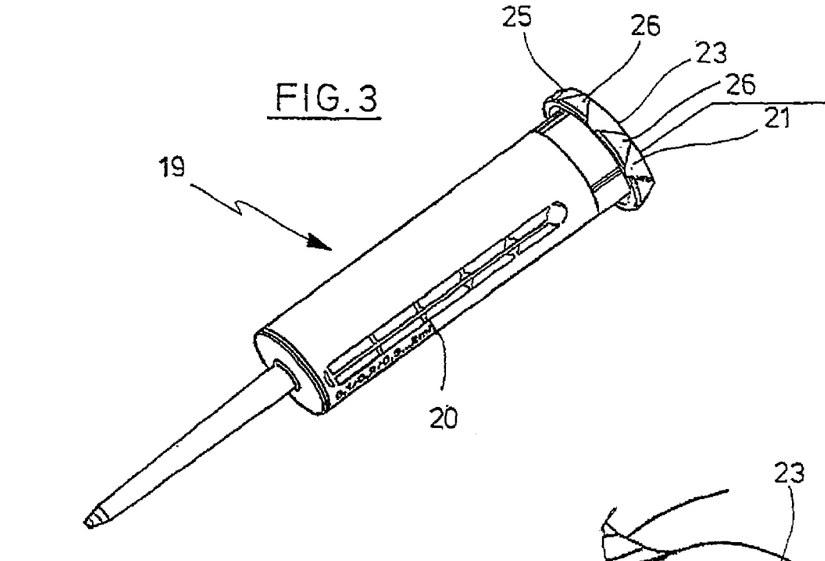

A syringe 19 to be connected to the metering device 1 has a syringe cylinder 20, shown enlarged in FIG. 3, with an annular fastening portion 21 in the form of a flange. The fastening portion 21 is dimensioned such that it fits into the accommodation 3 through the axial opening 4. At an upside of the fastening portion 21, there are axially projecting sensing surfaces 23. The sensing surfaces 23 have indentations 24, 24 on the upside 22. Number and arrangement of the indentations 24 encode a syringe 19 that has a certain volume. This is shown in detail in FIG. 4.

Figure 4:
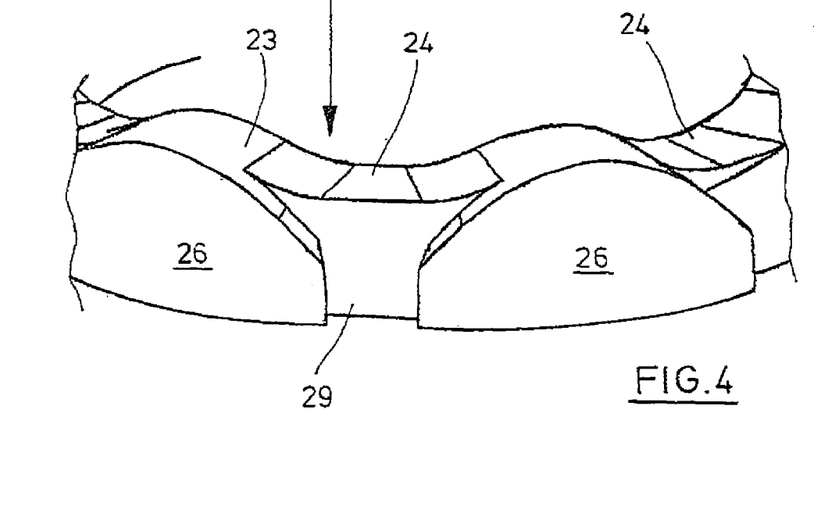

Several alignment noses 26 are present on the perimeter 25 of the fasting portion 21. The alignment noses 26 are uniformly distributed over the perimeter 25. They are formed by projections on the perimeter 25. The two side surfaces 27, 28 of every alignment nose 26 converge towards the upside. In the example, they are rounded. Between neighbouring alignment noses 26, there is a gap 29, which can receive an axial guiding means 7.

A plunger is disposed in the syringe cylinder 20, which is connected in one piece with a plunger rod 31 that projects out of the syringe cylinder 20.

Figure 2:
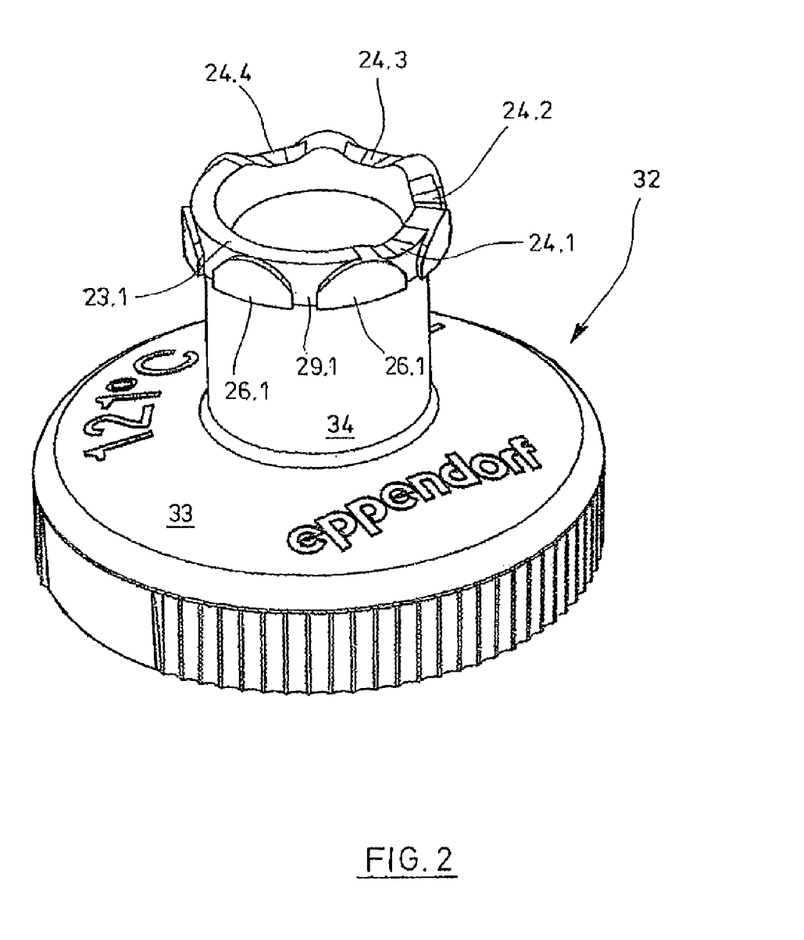

Further, big syringes can be connected to the metering device 1, whose syringe cylinder has a cross section which exceeds that of the accommodation 3. These syringe cylinders are connected at the upside via a clamping-, bayonet or screw joint to an adapter 32, which is also shown in FIG. 2.

The adapter 32 has a cap-like connecting portion 33, which bears a tube piece 34 on the upside, which corresponds to the upper end region of a syringe cylinder 20. The tube piece 34 has an annular fastening portion 21.1 with a sensing surface 23.1, which has indentations 24.1 to 24.4 which encode the big syringe received by the adapter. Further, alignment noses 26.1 with gaps 29.1 between them exist on the perimeter of the fastening portion 21.1. The adapter 32 is can be inserted into the accommodation 3 with its fastening portion 21.1.

Examples for syringes of the kind described above are described in EP 0 657 216 A2 and U.S. Pat. No. 5,620,661 A. The specifications concerning this in the above-mentioned documents are incorporated into the present application by reference.

Figure 5:
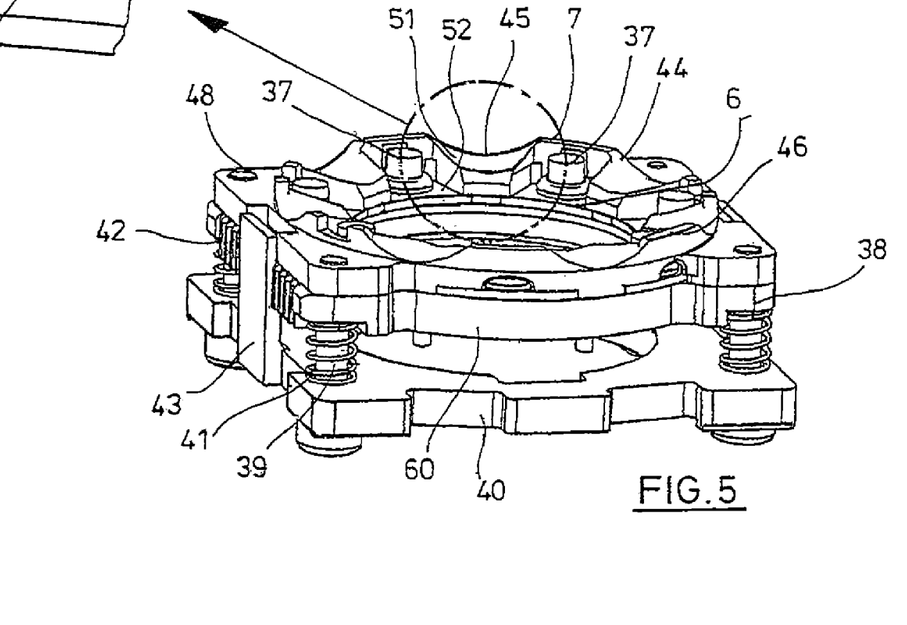
Figure 6:
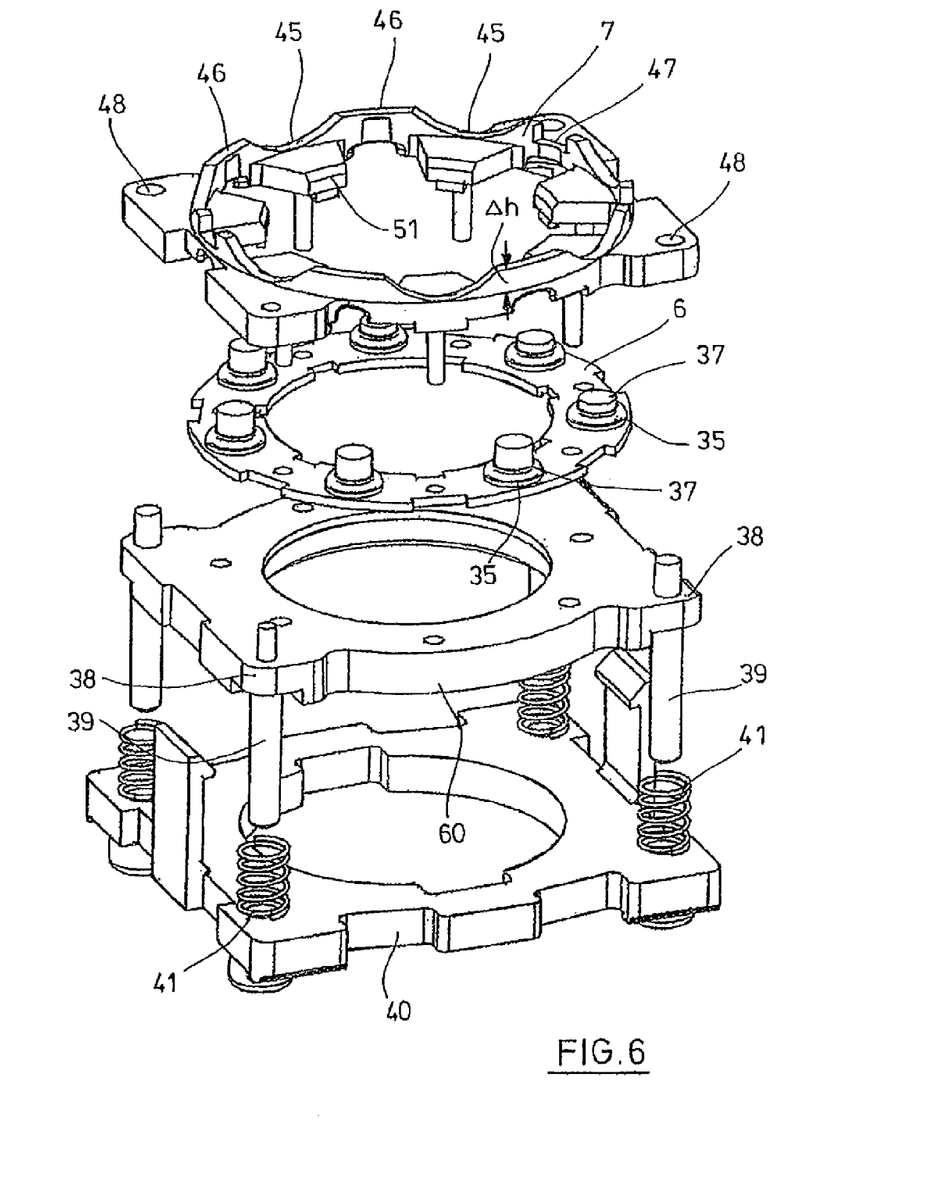

In FIGS. 5 and 6, an annular sensing device 6 and an associated annular guiding means 7 are shown, which are disposed on a mounting plate 60 that is positioned in the accommodation 3 of a metering device of the present invention. Whereas FIG. 5 shows this assembly group like as it is disposed in the metering device, the elements of the assembly group are shown individually in the exploded view of FIG. 6, for the sake of better illustration. According to FIGS. 5 and 6, the annular sensing device 6 features sensors 35 that are uniformly distributed over the perimeter. These have sensing means 37 in the form of sensing buttons which project from a basis surface 52 of the annular-disc shaped sensing device 6. The sensing means 37 are realised as knobs of an annular disc made of silicone, which sit on an annular circuit board with strip conductors on the side facing the annular disc. The knobs have a cavity which is opened at the side towards the strip conductors. On the bottom of the cavity, the knobs bear an electrically conductive material in the form of a conduction pill or a conductive paint. When a knob is axially compressed, the conductive material contacts two strip conductors and connects them electrically. A circuit is closed by this. After relief, the knob springs back elastically into an unloaded starting position.

An embodiment of this sensing device 6 is described in EP 0 657 216 A2 and U.S. Pat. No. 5,620,661 A. Their specifications concerning this are incorporated into the present application by reference.

The mounting plate 60 has four bores on laterally projecting edge regions 38, which are guided on stay bolts 39 which project from a holder plate 40. Spring means 41 in the form of helical springs are guided on the stay bolts 39 between the holder plate 40 and the mounting plate 60.

The sensing device 6 has a contact bank 42 on its edge, which is connected to the sensors. The contact bank 42 is connected to a flat cable 43, which is guided towards the analysing unit 16.

Figure 7:
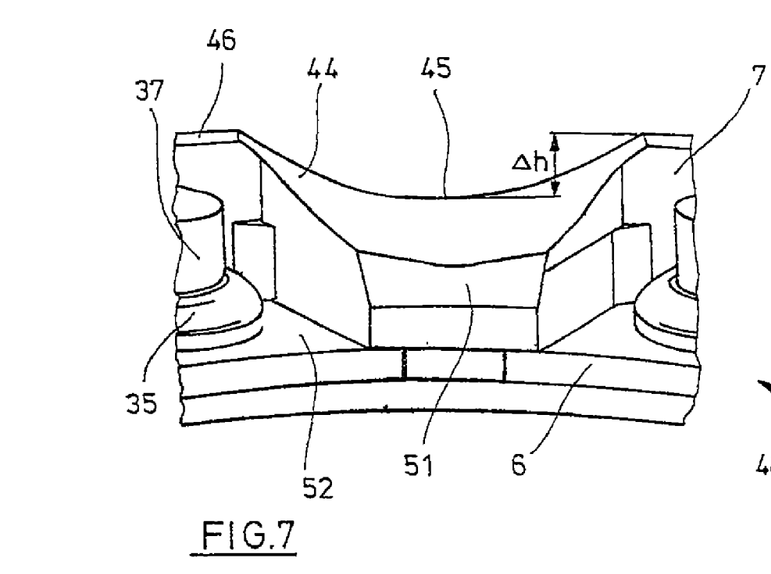

The annular guiding means 7 has a guiding contour 44 with indentations 45 and raised parts 46, shown in detail in FIG. 7, which shows the cut-out shown in a circle in FIG. 5 in an enlarged view. The raised parts 46 each have the same angular position as do the sensing means 37. The indentations 45 are at half angle between two neighbouring sensing means at a time. Three raised parts 46 are provided with recesses 47 on the upper edge, into which the upper ends of the lateral guiding means 60 of the metering device can engage.

The indentations 45 are rounded, so that they gradually ascend up to the raised parts 46. The indentations 45 have a form that is complementary to the upper sides of the alignment noses 26, 26.1. The raised parts 46 are flattened.

The indentations 45 all have the same level with respect to the basis surface 52 of the sensing device 6. The raised parts 46 are more distant from the basis surfaces 52. They all have the same distance from the basis surface 52. The difference $\Delta h$ between the distance of the raised part 46 from the basis surface and that of the indentation 25 from the basis surface is preferably 0.5 to 2 mm, particularly preferably 1 to 1.5 mm.

The annular sensing means 7 is likewise guided on the stay bolts 39 in bores in laterally projecting edge regions 48. At the inside, the guiding means 7 has abutment elements 51 in the form of console-shaped projections next to the indentations 45, which bear against the basis surface 52 of the sensing device 6.

The guiding means 7 and the sensing device 6 are rigidly connected to each other.

Figure 8:
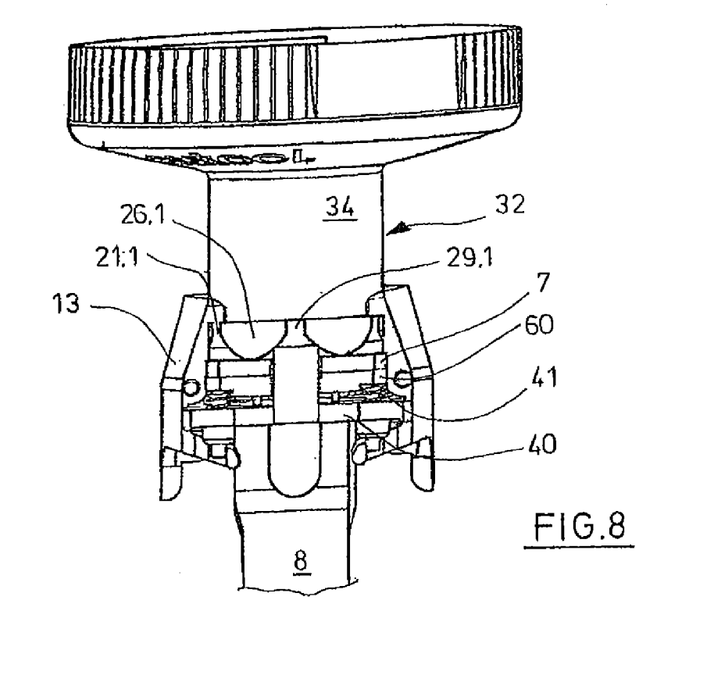
Figure 9:
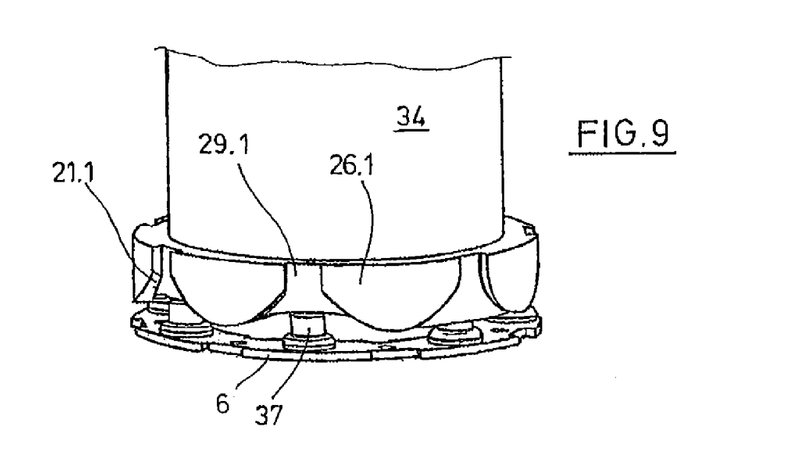

According to FIGS. 8 and 9 (guiding means 7 omitted for better representation), the adapter 32 put into the accommodation 3 is fixed in the pipette 1 by way of the gripping equipments 13. The lateral guiding means 60 engage into the recesses 47 between the alignment noses 26.1. The alignment noses 26.1 are disposed in the indentations of the annular guiding means 7. The spring means 42 are somewhat under spring tension.

The sensing surfaces 23 bear against the associated sensing means 37 and press the same together, so that they contact each other.

Figure 10:
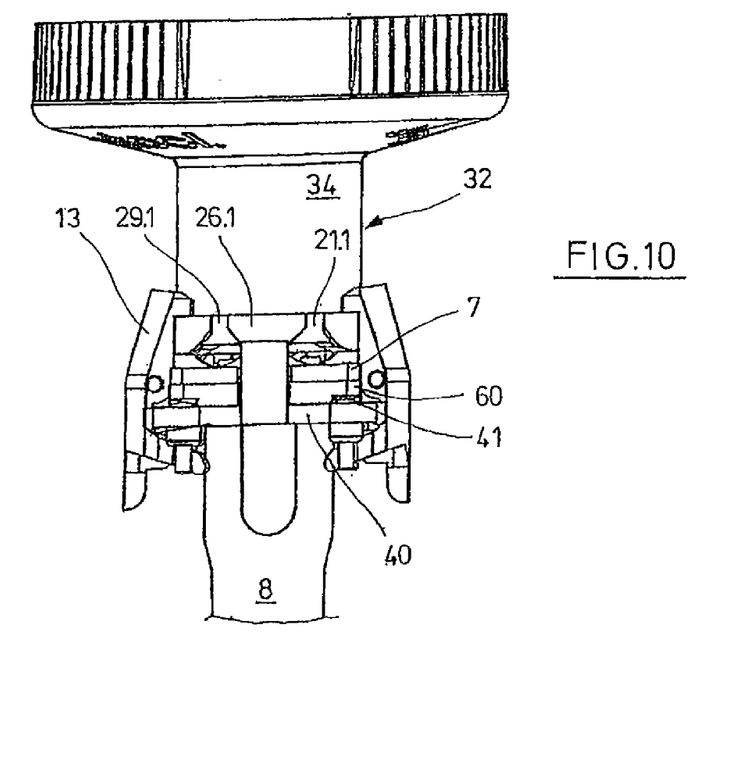
Figure 11:
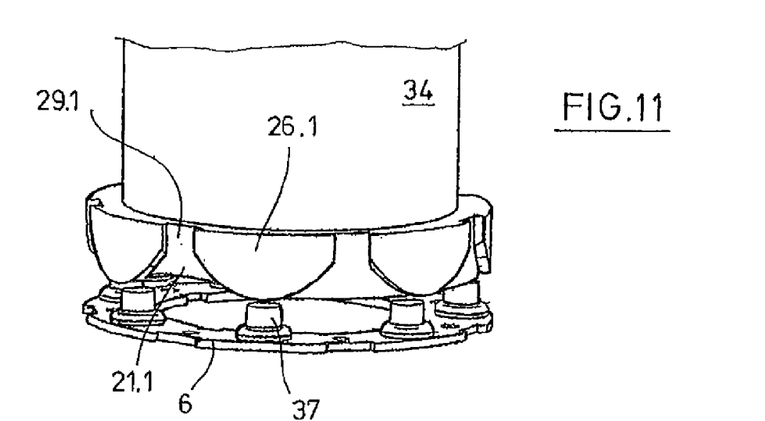

According to FIGS. 10 and 11 (sensing means 7 omitted for better illustration), the adapter 32 is twisted in the accommodation 3, so that the lateral guiding means 60 do no more engage into the recesses 47. Moreover, the alignment noses 26.1 sit on the raised parts 46 of the annular guiding means 7. Because the adapter 32 is to be kept in the accommodation 3 by way of the gripping equipments 13, the alignment noses 26.1 press the arrangement consisting of the annular guiding means 18 and the sensing device 6 upward, so that the spring means 41 continue to catch. In order to escape the very big force that occurs in this, the user of the metering device will rotate the syringe during the insertion, due to the contour of the alignment noses 26, 26.1 and the guiding means 7. When the adapter 32 is rotated in the accommodation 3, the sensing device 6 is moved by the sensing surfaces 23 of the adapter 32 in a distance, so that the sensing surfaces 32 do not shear off the sensing means 37. By the rotation, the alignment noses 26, 26.1 arrive then unavoidably in the indentations 25 of the guiding means, so that the correct regions of the sensing surface 23 are facing the sensing means 37 again, so that the same can acquire the code of the syringes 19 or the syringe adapters 19.1.

Thus, the sensing device 6 is not damaged at all. Only the sensing is put out of function due to the twisting of the adapter 32 out of the correct position.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A metering device for utilization with a syringe (19), said syringe including a syringe cylinder (20) a fastening portion (21) with at least one axially directed sensing surface (23) projecting from the upside, and at least one alignment nose projecting from the outer perimeter of the fastening portion (21), and a plunger with a plunger rod, the metering device comprising:
an accommodation (3) for the fastening portion (21) of the syringe cylinder (20), the accommodation (3) having an axial opening (4) for axially inserting the fastening portion (21) into a fastening position, a sensing device (6) disposed in the accommodation (3) with at least one sensing member (37) projecting from a basis surface (52) of the sensing device (6) facing the axial opening (4), for sensing the at least one sensing surface (23) of the fastening portion (21) inserted in a fastening position, at least one axial guiding member (7) for adjusting the at least one alignment nose (26) into an angular position with respect to rotation around the axis of the metering device, in which the syringe (19) is axially directed towards at least one sensing member with at least one sensing surface (23), an accommodation body (8) with a plunger accommodation and a further axial opening for axially inserting the plunger rod (31) into a fastening position, fastening devices (13, 14) for detachably holding fastening portion (21) and plunger rod (31) in their fastening positions in the accommodations (3) and in the plunger accommodation, and plunger adjustment devices (10) for shifting the accommodation body (8), wherein the axial guiding member (7) is present in the accommodation below the sensing device (6), wherein the guiding member (7) has a guiding contour (44) on the side that faces the axial opening (4), said guiding contour (44) has at least one indentation (45) for receiving at least one alignment nose (26) when the syringe (19) is disposed with fastening portion (21) and plunger rod (31) being in their fastening positions, and the at least one raised part (46) neighboring the indentation (45) has a distance from the basis surface (52) of the sensing device (6) greater than the at least one indentation (45), wherein the syringe (3) is adapted to be displaced with the at least one alignment nose (26) from the at least one indentation (45) to the at least one raised part (46).

2. A metering device according to claim 1, wherein the at least one axial guiding member (7) has a guiding bridge and/or a guiding groove in the axial direction.

3. A metering device according to claim 1, wherein plural sensing members (37) are distributed over the perimeter of the sensing device (6).

4. A metering device according to claim 1, wherein the sensing device (6) is supported in the accommodation by way of at least one spring member (41) acting axially against the displacement direction of the fastening portion (21).

5. A metering device according to claim 4, wherein the guiding member (7) is connected to the sensing device (6) and is supported in the accommodation (3) by way of the at least one spring member (41).

6. A metering device according to claim 1, wherein the fastening members (13, 14) have radially feedable gripping equipments for fixing the fastening portion (21) and the plunger rod (21) in the fastening positions.

7. A metering device according to claim 1, wherein the guiding member (7) is annular and the guiding contour (44) with several indentations (45) distributed over the perimeter and raised parts (46) disposed between them.

8. A metering device according to claim 1, wherein the number of the indentations (45) corresponds to the number of the sensing member (37).

9. A metering device according to one of claim 7 or 8, wherein the guiding contour (44) of the guiding member (7) gradually ascends between the indentations (45) and the raised parts (46).

10. A metering device according to claim 9, wherein the transitions between the indentations (45) and the raised parts (46) are ramp-shaped and/or rounded.

11. A metering device according to claim 1, wherein all the indentations (45) feature the same level with respect to the sensing device (6), and/or wherein all the raised parts (46) feature the same level with respect to the sensing device (6).

12. A metering device according to claim 1, with an analysing unit (16) and/or display unit (17) connected to the sensing device (6).

13. A metering device according to claim 1, wherein the plunger adjustment devices (10) are manually and/or motor driven.

14. A metering device according to claim 1, which can be held by the hand when metering.

15. A metering device according to claim 1, which is a stationary metering device.

16. A metering device according to claim 1, characterised in that the fastening portion of the syringe cylinder of the syringe (19) is annular.

17. A metering device according to claim 1, characterised in that the metering device is a pipette or a dispenser.

18. A metering device according to claim 1, characterised in that the sensing device (6) is annular.

19. A metering device according to claim 1, characterised in that the sensing surface (23) of the syringe features a flat surface vertical to the axis of the pipette, which has local indentations (50) with respect to this surface towards the downside, wherein a sensing member (37) of the metering device is actuated by the sensing surface (23) of the syringe opposite to it only then when the sensing surface does not have any local indentations (24) there and the at least one alignment nose (26) of the syringe is received in an indentation (45) of the guiding member (7).

20. A metering device according to claim 1, characterised in that the sensing surface (23) of the syringe features a flat surface vertical to the axis of the pipette, which has local raised parts raised against this surface towards the upside, wherein a sensing member (37) of the metering device opposite to the sensing surface is actuated by the sensing surface (23) of the syringe only then when the sensing surface has a local raised part there and the at least one alignment nose (26) of the syringe is accommodated in an indentation (45) of the guiding member (7).

21. A metering device according to claim 7, characterised in that the annular guiding member (7) has an outer ring with an inside diameter $R_1$, on which is disposed solely the guiding contour (44) with the indentations (45) and raised parts (46).

22. A metering device according to claim 21, characterised in that the sensing surface (23) of the syringe and the at least one sensing member (37) are disposed within the outer ring.

23. A metering device according to claim 22, characterised in that the sensing surface (23) of the syringe and the at least one sensing member (37) are disposed exclusively within the outer ring.

24. A metering device according to claim 7, characterised in that annular guiding members (7) have abutment elements (51) in addition, which bear two-dimensionally against a basis surface (52) of the sensing device (53).

25. A metering device according to claim 24, characterised in that the abutment elements (51) of the guiding member (7) are located within the outer ring having an inside diameter $R_1$.

26. A metering device according to claim 1, characterised in that a syringe (19) is received by the fastening devices (13, 14) only when at least one alignment nose (26) of the syringe (19) is received in the at least one indentation (45) of the guiding member (7).

27. A metering device and syringe, said syringe (19) including a syringe cylinder (20) a fastening portion (21) with at least one axially directed sensing surface (23) projecting from the upside, and at least one alignment nose projecting from the outer perimeter of the fastening portion (21), and a plunger with a plunger rod, the metering device having an accommodation (3) for the fastening portion (21) of the syringe cylinder (20), the accommodation (3) having an axial opening (4) for axially inserting the fastening portion (21) into a fastening position, a sensing device (6) disposed in the accommodation (3) with at least one sensing member (37) projecting from a basis surface (52) of the sensing device (6) facing the axial opening (4), for sensing the at least one sensing surface (23) of the fastening portion (21) inserted in a fastening position, at least one axial guiding member (7) for adjusting the at least one alignment nose (26) into an angular position with respect to rotation around the axis of the metering device, in which the syringe (19) is axially directed towards at least one sensing member with at least one sensing surface (23), an accommodation body (8) with a plunger accommodation and a further axial opening for axially inserting the plunger rod (31) into a fastening position, fastening devices (13, 14) for detachably holding fastening portion (21) and plunger rod (31) in their fastening positions in the accommodations (3) and in the plunger accommodation, and plunger adjustment devices (10) for shifting the accommodation body (8), wherein the axial guiding member (7) is present in the accommodation below the sensing device (6), wherein the guiding member (7) has a guiding contour (44) on the side that faces the axial opening (4), said guiding contour (44) has at least one indentation (45) for receiving at least one alignment nose (26) when the syringe (19) is disposed with fastening portion (21) and plunger rod (31) being in their fastening positions, and the at least one raised part (46) neighboring the indentation (45) has a distance from the basis surface (52) of the sensing device (6) greater than the at least one indentation (45), wherein the syringe (3) is adapted to be displaced with the at least one alignment nose (26) from the at least one indentation (45) to the at least one raised part (46).

* * * * *